United States Patent [19]

Cainelli et al.

[11] Patent Number: 5,721,360
[45] Date of Patent: Feb. 24, 1998

[54] PROCESS FOR THE PREPARATION OF A THIAZOLINE-AZETIDINONE

[75] Inventors: Gianfranco Cainelli; Achille Umani Ronchi; Michele Contento; Mauro Panunzio, all of Bologna; Sergio Sandri, Forli'; Marco Da Col, Bologna; Leone Dall'Asta, Pavia, all of Italy

[73] Assignee: Biochimica OPS Spa, Milan, Italy

[21] Appl. No.: 656,979

[22] Filed: Jun. 6, 1996

Related U.S. Application Data

[63] Continuation of PCT/EP95/03975, Oct. 9, 1995

[30] Foreign Application Priority Data

Oct. 10, 1994 [IT] Italy .................... MI94A2056

[51] Int. Cl.$^6$ .................................. C07D 205/12
[52] U.S. Cl. ................................................ 540/353
[58] Field of Search ................................. 540/353

[56] References Cited

PUBLICATIONS

Journal American Chemical Society 92 (8), pp. 2575–2586 (1970), Cooper, R.D.G., et al, "Structural studies on penicillin derivatives".

Chemical Abstracts 87 (9), No. 68339u (1977) Tanida, H., et al, "Ring fission and cyclization of thiopenicillin oxides", p. 2552.

*Primary Examiner*—Joseph K. McKane
*Attorney, Agent, or Firm*—Michael N. Meller

[57] ABSTRACT

The present invention refers to process for the preparation of a tiazoline-azetidinone of formula I

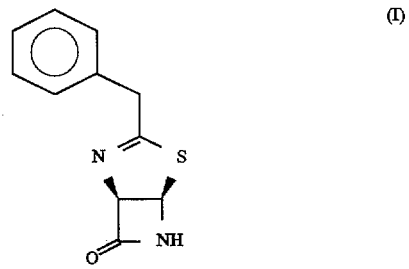

which comprises N-protecting in position 1 of (3S,4S)-3-phenylace tamido-4-acetoxy-azetidin-2-one, converting the product thus obtained into the corresponding thioamide and subsequently ciclyzing and deprotecting.

13 Claims, No Drawings

PROCESS FOR THE PREPARATION OF A THIAZOLINE-AZETIDINONE

This is a continuation of PCT/EP95/03975 filed Oct. 9, 1995.

The present invention concerns a process for the preparation of (1R,5R)-3-benzyl-4,7-diaza-2-thiabicyclo[3.2.0]hept-3-en-6-one of formula I

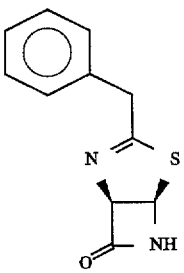

hereinbelow indicated "thiazoline-azetidinone".

The thiazoline-azetidinone of formula I has been previously described by R. D. G. Cooper and F. L. Josè in J. Am. Chem. Soc. 94, 1021 (1972).

The obtention of tiazoline-azetidinone of formula I using easy methods and easy to carry out represents a great success, because, for its great versatility, this product is a key intermediate in the preparation of semisynthetic cephalosporins.

It has now been found a method which allows to prepare in three or even two steps the thiazoline-azetidinone of formula I starting from a product easily available.

More particularly, it has been found that, using as starting material (3S,4S)-3-phenylacetamido-4-acetoxy-azetidin-2-one it is possible to obtain the thiazoline-azetidinone by protecting the nitrogen in position 1, converting the amide into the corresponding thioamide and cyclizing with consequent deprotection.

Moreover it has been found that the protection in position 1 and the transformation of the carbonyl group of the amide into a thiocarbonyl group may be carried out sequentially in one pot with the consequent possibility to remarkably increase of the yields in product of formula I.

Thus, according to one of its aspects, the present invention provides a process for the preparation of the thiazoline-azetidinone of formula I, which comprises protecting the nitrogen in position 1 of the (3S,4S)-3-phenylacetamido-4-acetoxy-azetidin-2-one of formula II

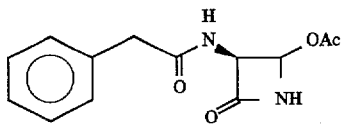

in which Ac represents acetyl, then treating the N-protected product thus obtained of formula III

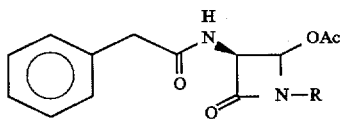

in which Ac is as above defined and R represents a N-protecting group, with an inorganic sulfide to obtain the corresponding thioamide of formula IV

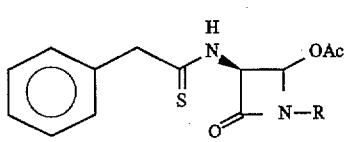

in which Ac and R are as above defined, cyclizing the compound IV thus obtained in the presence of an organic base and deprotecting the N-protected tiazoline-azetidinone of formula V

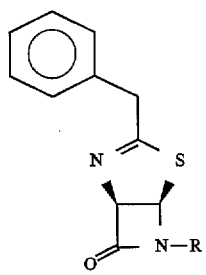

in which R is as above defined.

The term "N-protecting group" indicates, in the sense of the present invention, any group currently used in the chemistry of cephalosporins to avoid that a primary or secondary amide group gives side reactions. The term N-protected, referred to a product, concerns the product in which the amide group as above defined is substituted with a N-protecting group.

The characteristics of the N-protecting group, according to the present invention, are such to allow:

the transformation of the amide of formula III into the corresponding thioamide of formula IV;

the cyclization of the thioamide of formula IV into the N-protected thiazoline-azetidinone of formula V;

the N-deprotection of the compound of formula V to obtain the thiazoline-azetidinone of formula I, without inducing other modifications of the compounds of formula II, III, IV and V.

It has been found that the N-protecting group, which meets the above mentioned requirements, may be silyl, benzyl substituted or acyl.

The preferred N-protecting groups R are trialkylsilanes, such as trimethylsilyl, triethylsilyl, ($C_2$–$C_5$) alkyldimethylsilyl, particularly the tert-butyldimethylsilyl group (TBDMS).

The introduction of the N-protecting group occurs by treating the (3S,4S)-4-acetoxy-3-phenylacetamido-azetidin-2-one of formula II with a compound of formula VI

R-X (VI)

in which R is as above defined and X represents a halogen, preferably chlorine, a trifluoromethanesulfonyl or sulfonyl group, optionally in the presence of imidazole, in an organic solvent, preferably a halogenated hydrocarbon, in the presence of a condensing agent. The preferred compound of formula VI is tert-butyldimethylchlorosilane, the halogenated solvent is dichloromethane or 1,1,1-trichloroethane and the condensing agent is 4-dimethylaminopyridine, or a mixture of 4-dimethylaminopyridine and pyridine in the molar ratio 1:10.

Thus, the N-protected (3S,4S)-4-acetoxy-3-phenylacetamido-azetidin-2-one of formula III is obtained in very high yields and may be isolated according to the conventional techniques, for example by extraction with a suitable solvent and evaporation of such a solvent.

The preparation of the thioamide of formula IV, namely the transformation of carbonyl of the phenylacetamido group of the compound of formula III into the corresponding thiocarbonyl, occurs by treatment of the N-protected (3S, 4S)-4-acetoxy-3-phenylacetamido-azetidin-2-one of formula III with an inorganic sulfide, for example with hydrogen sulfide in the presence of phosphorus pentachloride and of a condensing agent.

The reaction with hydrogen sulfide and phosphorus pentachloride occurs in an organic solvent at a temperature from −70° C. to −40° C. and is stopped by addition to the mixture of water and ice. Preferably, starting from (3S,4S)-4-acetoxy-3-phenylacetamido-1-tert-butyldime thylsilyl-azetidin-2-one (III, R=TBDMS) the reaction occurs in a halogenated solvent such as dichloromethane or 1,1,1-trichloroethane in the presence of N,N-dimethylaniline at a temperature from −55° C. to −45° C.

Thus the N-protected (3S,4S)-4-acetoxy-3-phenylethanethioylamino-azetidin-2-one is obtained, which may be isolated according to the conventional techniques. For example, the (3S,4S)-4-acetoxy-3-phenyl ethanethioylamino-1-tert-butyldimethylsilyl-azetidin-2-one (IV, R=TBDMS) is isolated by neutralization of the reaction mixture with a base such as sodium hydrogen carbonate, extraction of the reaction product with a suitable solvent, preferably halogenated such as dichloromethane or 1,1,1-trichloroethane and evaporation of the solvent.

The reactions of N-protection and transformation of the carbonyl group into the corresponding thiocarbonyl group, namely the preparation of the compounds of formula III and IV, may take place in one pot. In that case also the treatment of the reaction mixture containing the N-protected (3S,4S)-4-acetoxy-3-phenylacetamido-azetidin-2-one of formula III with hydrogen sulfide occurs by using the same solvent of the N-protecting reaction.

The cyclization of the thioamide IV to give the (1R,5R)-3-benzyl-4,7-diaza-2-thiabicyclo[3.2.0]hept-3-en-6-one N-protected in position 7, of formula V, occurs by treatment of the product IV with an organic base, preferably a tertiary amine, such as triethylamine, in an inert organic solvent, such as benzene or toluene.

The reaction occurs at a temperature of 70°+130° C. and may be carried out at reflux; the product of formula V thus obtained may be isolated according to the conventional techniques, for example by extraction with a suitable solvent.

Finally, the (1R,5R)-3-benzyl-4,7-diaza-2-thiabicyclo [3.2.0]hept-3-en-6-one N-protected in position 7 is deprotected according to known methods, as described by T. W. Greene and P. G. M. Wuts in Protective Groups in Organic Synthesis—Wiley 1991.

According to a preferred method, when the N-protecting group is a silylating group, particularly a tert-butyldimethylsilyl group, the cyclization of the thioamide of formula IV involves the simultaneous deprotection of the amine in position 7 and the isolation of the thioazoline-azetidinone of formula I.

The isolation of the thiazoline-azetidinone of formula I occurs, for example, by extraction with ethyl acetate and concentration under vacuum of the organic phase. The crude product thus obtained is purified according to the conventional techniques to give the pure thiazoline-azetidinone of formula I in very high yields.

The thioamide N-protected on the azetidine nitrogen, of formula IV, is a new product which represents another aspect of the present invention.

According to a preferential aspect, the present invention concerns the preparation of the thiazoline-azetidinone of formula I in only three or two steps, without isolating the compound of formula V, using tert-butyldimethylsilyl (TBDMS) as protecting group R according to the following schema, in which the compounds in brackets are not isolated from the reaction mixture:

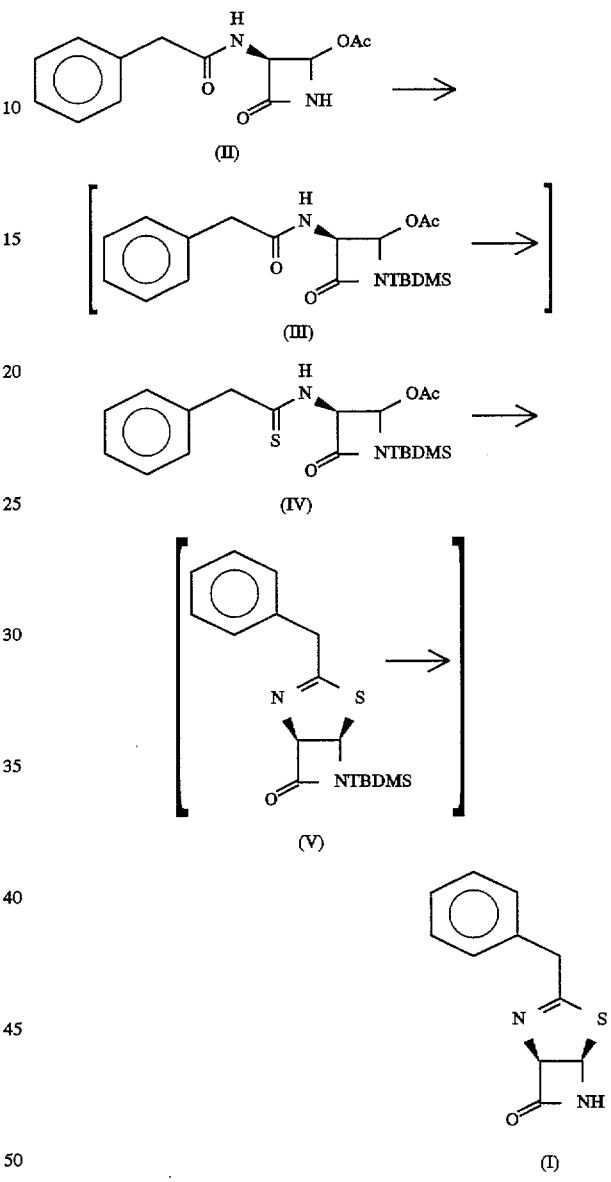

Such a preferred procedure comprises treating the (3S, 4S)-4-acetoxy-3-phenylacetamido-azetidin-2-one (II) with tert-butyldimethyl chlorosilane in the presence of 4-dimethylaminopyridine and, optionally, of pyridine in an organic solvent, isolating the (3S,4S)-4-acetoxy-3-phenylacetamido-1-tert-butyldimethylsilyl-azetidin-2-one (III) thus obtained and treating with an inorganic sulfide to obtain (3S,4S)-4-acetoxy-3-phenylethanethioylamino-1-tert-butyldime thylsilyl-azetidin-2-one (IV) and treating this compound with a base in an organic solvent at a temperature of 70°+130° C.

The same preferred process may be carried out in only two steps. In that case the (3S,4S)-4-acetoxy-3-phenylacetamido-azetidin-2-one (II) is treated with tert-butyldimethylchlorosilane in the presence of 4-dimethylaminopyridine and, optionally, of pyridine in an organic solvent, then the reaction mixture is treated with an inorganic sulfide and the (3S,4S)-4-acetoxy-3-phenylethanethioylamino-1-tert-butyldimethylsilyl-azetidin-2-one (IV) is isolated, and finally this compound is treated with a base in an organic solvent at a temperature of 70°+130° C.

The operations are carried out as defined above. Particularly, as inorganic sulfide, hydrogen sulfide may be used in the presence of phosphorus pentachloride at low temperature (about −50° C.) and as condensing agent a tertiary amine like triethylamine is preferably used.

As solvents, dichloromethane or 1,1,1-trichloroethane are preferably used for the reaction with tert-butyldimethylchlorosilane and toluene for the cyclization and simultaneous N-deprotection.

The (3S,4S)-4-acetoxy-3-phenylethanethioylamino-1-tert-butyldime thylsilyl-azetidin-2-one (IV, R=TBDMS) represents, among the products of formula IV, the preferred compound.

The (3S,4S)-4-acetoxy-3-phenylacetamido-azetidin-2-one (II) used as starting material in the process of the present invention is an easily accessible product which may be obtained from the (3s,4S)-4-acetoxy-3-benzyloxycarbonylamino-azetidin-2-one, as described by Andreoli et al. in Tetrahedron 47, 9061 (1991).

The following examples illustrate the invention without, however, limiting it.

PREPARATION

To a solution of 0.55 g (2 moles) of (3S,4S)-4-acetoxy-3-benzyl oxycarbonylamino-azetidin-2-one in 2 ml of anisole 0.40 g (3 mmoles) of anhydrous aluminum chloride are added at 20° C., by controlling the reaction by TLC (eluent: ethyl acetate/methanol=95/5 v/v). When the reaction is over, the mixture is filtered off and the filtered solution is concentrated under vacuum to obtain a residue of 0.260 g consisting of crude (3S,4S)-4-acetoxy-3-amino-azetidin-2-one. The residue is taken up with 30 ml of ethyl acetate and to the resulting solution 0.31 g (3 moles) of triethylamine and, afterwards, 0.695 g (4.5 mmoles) of phenylacetyl chloride are added. The mixture is stirred for 6 hours at 20°+25° C., then it is concentrated under vacuum to obtain a residue which is taken up with ethyl acetate and subjected to a purification on a silica gel column (eluent: ethyl acetate). Thus, 0.165 g of (3S,4S)-4-acetoxy-3-phenylacetamido-azetidin-2-one (II) is obtained.

$^{1}$H-NMR (CDCl$_{3}$, ppm): 2.1 (s, 3H); 3.6 (s, 2H); 4.7 (d, 1H); 5.8 (s, 1H); 6.53 (d, 1H); 7.13 (s, 1H); 7.32 (m, 5H).

EXAMPLE 1

(a) To a solution of 1.5 g of (3S,4S)-4-acetoxy-3-phenylacetamido-azetidin-2-one in 100 ml of dichloromethane, at room temperature and under inert atmosphere, 0.069 g (0.56 moles) of 4-dimethylamino pyridine and 0.5 ml of pyridine are added. To this mixture 0.907 g (6 mmoles) of tert-butyldimethylchlorosilane dissolved in 10 ml of anhydrous dichloromethane are slowly added. The mixture is let under stirring for about 24 hours, then a phosphate buffer at pH 7.5 is added. The organic phase is extracted with dichloromethane and the dichloromethane phase is washed with a saturated solution of sodium chloride, dried over anhydrous sodium sulfate and concentrated under vacuum. Thus, essentially pure (3S,4S)-4-acetoxy-3-phenylacetamido-1-tert-butyldimethylsilyl-azetidin-2-one (III, R=TBDMS) is obtained in quantitative yield.

$^{1}$H-NMR (CDCl$_{3}$, ppm): 0.25 (d, 6H); 1.0 (s, 9H); 2.1 (s, 3H); 3.6 (s, 2H); 4.4 (d, 1H); 6.1 (s, 1H); 6.2 (s, 1H); 7.3 (m, 5H).

(b) To 0.376 g (1 mmole) of the compound obtained in step (a) dissolved in 8 ml of dichloromethane, at the temperature of −50° C., 0.35 ml (2.5 mmoles) of N,N-dimethylaniline and 0.229 g (1.1 mmoles) of phosphorus pentachloride are added. The temperature is maintained constant at −50° C. for 3 ore, then hydrogen sulfide is bubbled thereinto. Then the temperature is let to reach 0° C. and again the hydrogen sulfide is bubbled for 45 minutes. Ice and sodium hydrogen carbonate are added, the mixture is extracted with dichloromethane, dried over anhydrous sodium sulfate and concentrated under vacuum. The residue is purified by silica gel column chromatography (eluent: cyclohexane/ethyl acetate=6/4 v/v) to obtain the (3S,4S)-4-acetoxy-3-phenylethanethioylamino-1-tert-butyldimethylsilyl-azetidin-2-one (IV, R=TBDMS).

$^{1}$H-NMR (CDCl$_{3}$, ppm): 0.25 (d, 6H); 0.98 (s, 9H); 2.14 (s, 3H); 4.1 (s, 2H); 5.1 (d, 1H); 6.2 (s, 1H); 7.3 (m, 5H); 8.0 (d, 1H).

(c) To a solution of 0.16 g (0.4 mmoles) of silylated thioamide obtained in step (b) in 10 ml of toluene, 0.1 ml (0.4 mmoles) of triethylamine are added. The reaction mixture is refluxed for 1 hour, then the temperature is let to reach the room temperature and the mixture is strongly stirred overnight. After addition of water, the mixture is extracted with ethyl acetate, dried over anhydrous sodium sulfate and concentrated under vacuum. The crude product obtained from the reaction is purified by chromatography on a silica gel column (eluent: cyclohexane/ethyl acetate=1/1 v/v).

Yield: 98% of the compound of formula I.

$^{1}$H-NMR (CDCl$_{3}$, ppm): 3.9 (q, 2H); 5.45 (d, 1H); 6.0 (dd, 1H); 6.69 (broad s, 1H); 7.3 (m, 5H).

EXAMPLE 2

(a) To a solution of 5.24 g (20 moles) of (3S,4S)-4-acetoxy-3-phenylacetamido-azetidin-2-one in 60 ml of anhydrous dichloromethane, at room temperature and under inert atmosphere, 4.9 g (40 mmoles) of 4-dimethylaminopyridine and 4.5 g (30 mmoles) of tert-butyldimethyl clorosilane are added. After a strong stirring for 16 hours, at −50° C., 6.25 ml (50 mmoles) of N,N-dimethylaniline and 4.58 g (22 mmoles) of phosphorus pentachloride are added. The reaction mixture is stirred at −50° C. for 3 hours, then hydrogen sulfide is bubbled for about 30 minutes. The temperature is let to reach about 20° C., then the reaction mixture is treated with an aqueous solution of sodium hydrogen carbonate. The mixture is extracted with dichloromethane, the organic phase is washed with a saturated aqueous solution of sodium chloride, dried over anhydrous sodium sulfate and concentrated under vacuum. The thioamide is purified by silica gel column chromatography (eluent: cyclohexane/ethyl acetate=6/4 v/v). The pure (3S,4S)-4-acetoxy-3-phenylethanethioylamino-1-tert-butyldimethyl silyl-azetidin-2-one is thus obtained.

$^{1}$H-NMR (CDCl$_{3}$, ppm): 0.25 (d, 6H); 0.98 (s, 9H); 2.14 (s, 3H); 4.1 (s, 2H); 5.1 (d, 1H); 6.2 (s, 1H); 7.3 (m, 5H); 8.0 (d, 1H).

(b) Starting from the silylated thioamide obtained in step (a), by operating as described in the Example 1(c), the thiazoline-azetidinone I is obtained in a global yield of 70%.

We claim:
1. A process for the preparation of thiazoline-azetidinone of formula I

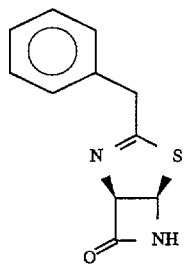
(I)

which comprises a) treating the (3S,4S)-4-acetoxy-3-phenylacetamido-azetidin-2-one of formula II

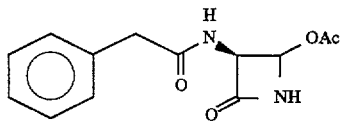
(II)

in which Ac represents an acetyl group, with the compound of formula VI

R-X    (VI)

in which R represents a silyl, benzyl or acyl group and X represents a halogen atom, a trifluoromethanesulfonyl or sulfonyl group, optionally in the presence of imidazole, to obtain the corresponding N-protected compound of formula III

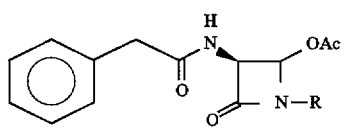
(III)

b) treating the N-protected compound III with an inorganic sulfide to obtain the corresponding thioamide of formula IV

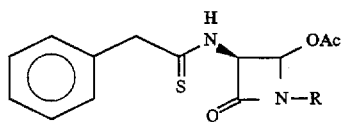
(IV)

in which Ac and R are as above defined;

c) cyclizing the compound IV thus obtained in the presence of an organic base to obtain the N-protected thiazoline-azetidinone of formula V

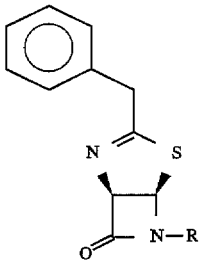
(V)

d) removing the R group from the compound V to obtain the desired compound I.

2. A process according to claim 1, in which the compound RX of formula VI is the tert-butyldimethylchlorosilane.

3. A process according to claim 1, in which the reaction of N-protection is carried out in dichloromethane or 1,1,1-trichloroethane.

4. A process according to claim 1, in which (3S,4S)-4-acetoxy-3-phenylacetamido-azetidin-2-one is treated with tert-butyldimethyl chlorosilane in the presence of 4-dimethylaminopyridine in an organic solvent and the (3S,4S)-4-acetoxy-3-phenylacetamido-1-tert-butyldimethylsilyl-azetidin-2-one (III) is isolated.

5. A process according to claim 4, in which the reaction of N-protection with tert-butyldimethylchlorosilane is carried out in the presence of 4-dimethylaminopyridine and pyridine in the molar ratio 1:10.

6. A process according to claim 4, in which the compound IV is treated with an inorganic sulfide to obtain the (3S,4S)-4-acetoxy-3-phenylethanethioylamino-1-tert-butyldimethylsilyl-azetidin-2-one (V) and this compound is treated with a base in an organic solvent at a temperature of 70°–130° C.

7. A process according to claim 1, in which the treatment with an inorganic sulfide is carried out in the reaction mixture containing the compound III without isolating it.

8. A process according to claim 1, in which the treatment for removal of the R group is made on the reaction mixture containing the compound V without isolating it.

9. A process according to claim 1, in which a tertiary amine is used for the cyclization.

10. A process according to claim 9, in which the tertiary amine is triethylamine.

11. A process according to claim 4, in which the treatment with an inorganic sulfide is carried out in the reaction mixture containing the compound III without isolating it.

12. A process according to claim 6, in which the treatment for removal of the R group is made on the reaction mixture containing the compound V without isolating it.

13. A process according to claim 8, in which a tertiary amine is used for the cyclization.

* * * * *